(12) United States Patent
Hinrichsen et al.

(10) Patent No.: US 11,210,479 B2
(45) Date of Patent: Dec. 28, 2021

(54) WIRELESS TRACKING OF DEVICE CHARACTERISTICS

(71) Applicant: Medtronic, Inc., Minneapolis, MN (US)

(72) Inventors: Ross D. Hinrichsen, Minneapolis, MN (US); William C. Harding, Chandler, AZ (US); Peter N. Braido, Linwood, MN (US); Mina S. Fahim, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/453,394

(22) Filed: Jun. 26, 2019

(65) Prior Publication Data

US 2020/0410176 A1 Dec. 31, 2020

(51) Int. Cl.
*A61B 90/00* (2016.01)
*G06K 7/10* (2006.01)
*G06K 19/07* (2006.01)
*G16H 10/65* (2018.01)

(52) U.S. Cl.
CPC .......... *G06K 7/10316* (2013.01); *A61B 90/02* (2016.02); *A61B 90/08* (2016.02); *A61B 90/39* (2016.02); *G06K 19/0723* (2013.01); *G16H 10/65* (2018.01); *A61B 2090/397* (2016.02)

(58) Field of Classification Search
CPC ............ G06K 7/10316; G06K 19/0723; A61B 90/39; A61B 90/02; A61B 2034/2051; A61B 90/98; A61B 18/00; A61B 90/37

USPC ........................................................ 340/10.1
See application file for complete search history.

(56) References Cited

U.S. PATENT DOCUMENTS

| | | | |
|---|---|---|---|
| 6,198,968 B1 * | 3/2001 | Prutchi | A61N 1/37 128/901 |
| 6,575,933 B1 * | 6/2003 | Wittenberger | A61B 18/02 128/898 |
| 8,321,019 B2 | 11/2012 | Esch et al. | |
| 8,636,729 B2 | 1/2014 | Esch et al. | |
| 8,721,634 B2 | 5/2014 | Esch et al. | |
| 9,521,961 B2 | 12/2016 | Silverstein et al. | |
| 9,861,440 B2 | 1/2018 | van der Weide et al. | |
| 9,872,729 B2 | 1/2018 | van der Weide et al. | |
| 9,918,792 B1 | 3/2018 | Boveja et al. | |
| 9,987,097 B2 | 6/2018 | van der Weide et al. | |

(Continued)

*Primary Examiner* — Vernal U Brown
(74) *Attorney, Agent, or Firm* — Christopher & Weisberg, P.A.

(57) ABSTRACT

A system for assessing at least one characteristic of a device within a recipient is provided. The system includes a device removably insertable into the recipient where the device includes at least one of a treatment element and implant, and at least one wireless tag positioned within at least one portion of the device. The system includes a tracking device that includes processing circuitry configured to: if the device is inserted into the recipient, interrogate the at least one wireless tag positioned within at least one portion of the device; determine at least one characteristic of at least one portion of the device in three dimensional space based at least in part on the interrogation of the at least one wireless tag; and cause the at least one characteristic of the at least one portion of the device relative to the recipient to be indicated.

20 Claims, 8 Drawing Sheets

(56) References Cited

U.S. PATENT DOCUMENTS

| | | |
|---|---|---|
| 2005/0012610 A1* | 1/2005 | Liao .................... A61B 5/0008 |
| | | 340/539.12 |
| 2007/0049999 A1 | 3/2007 | Esch et al. |
| 2007/0050000 A1 | 3/2007 | Esch et al. |
| 2007/0078334 A1* | 4/2007 | Scully ..................... A61B 5/06 |
| | | 600/424 |
| 2007/0179575 A1 | 8/2007 | Esch et al. |
| 2009/0082722 A1 | 3/2009 | Munger et al. |
| 2010/0275934 A1* | 11/2010 | Keren .................... A61B 90/39 |
| | | 128/899 |
| 2013/0116679 A1 | 5/2013 | Van der Weide et al. |
| 2015/0272654 A1 | 10/2015 | Esch et al. |
| 2016/0015453 A1 | 1/2016 | van der Weide et al. |
| 2016/0157868 A1* | 6/2016 | Tillman ........... A61B 17/12136 |
| | | 606/194 |
| 2017/0095315 A1 | 4/2017 | van der Weide et al. |
| 2018/0042517 A1 | 2/2018 | van der Weide et al. |
| 2018/0078309 A1 | 3/2018 | Van der Weide et al. |
| 2018/0125579 A1 | 5/2018 | Van der Weide et al. |
| 2019/0262056 A1* | 8/2019 | Yang ..................... A61B 18/02 |
| 2019/0336665 A1* | 11/2019 | Frost .................. A61B 17/1204 |

* cited by examiner

FIG. 6
Recapture begins

FIG. 5
Valve positioned too deep

FIG. 8
Valve fully recaptured

FIG. 7
Partially recaptured

WIRELESS TRACKING OF DEVICE CHARACTERISTICS

CROSS-REFERENCE TO RELATED APPLICATION n/a

FIELD

The present invention generally relates medical devices and treatments, and in particular, to a method and system for determining at least one characteristic of a medical device relative to a recipient such as position, location and/or orientation of the medical device.

BACKGROUND

In many non-invasive or minimally invasive surgical and treatment procedures, navigating a medical device within a recipient's (e.g., person receiving medical treatment and/or medical procedure) body can be very challenging. Navigation systems are frequently used to help the user identify the location of the medical device and to steer the medical device to the target treatment location. For example, navigation is an important tool in many electrophysiological (EP) procedures because it helps the user understand the placement of the medical device within the cardiac space. Additionally, navigation is often used to place medical devices at areas targeted for thermal treatment and/or ablation.

When the medical device is a focal catheter, for instance, the ablating surface may be directly imaged on the navigation system and there is a close coupling between the navigation and the delivered therapy. However, other medical devices, such as balloon catheters, may have more complex geometry, and navigation electrodes on the device may not exactly correlate with the ablating surface (e.g., the surface of the balloon). Additionally, placement of these complex geometry devices may be difficult to infer from fluoroscopic imaging or navigation systems relative to the targeted tissue regions.

Further, the current standard of care during atrial fibrillation intervention procedures may require fluoroscopy to visualize the catheter and anatomy of the recipient. The radiation of the imaging as well as the need for dye injection for occlusion assessment poses a risk to the recipient's health. The use of fluoroscopy also carries the risk of additional radiation for the physician and staff, and requires the use of heavy lead aprons leading to significant orthopedic issues.

SUMMARY

The techniques of this disclosure generally relate to a method and system for determining at least one characteristic of a device such as an ablation catheter, delivery system of a therapy, and/or implant relative to an individual such as position, location and/or orientation of the device, therapy, and/or implant. The device may include an ablation catheter, delivery system of an implant/therapy, and/or the implant itself.

According to one aspect of the invention, a system for assessing at least one characteristic of a device within a recipient is provided. The system includes a device removably insertable into the recipient where the device includes at least one of a treatment element and implant, and at least one wireless tag positioned within at least one portion of the device. The system includes a tracking device that includes processing circuitry configured to: if the device is inserted into the recipient, interrogate the at least one wireless tag positioned within at least one portion of the device; determine at least one characteristic of at least one portion of the device in three dimensional space based at least in part on the interrogation of the at least one wireless tag; and cause the at least one characteristic of the at least one portion of the device relative to the recipient to be indicated.

According to one or more embodiments of this aspect, the processing circuitry is further configured to determine at least one of an impedance quantity and distance between wireless tags by assessing a signal strength and response time. According to one or more embodiments of this aspect, the impedance quantity between the wireless tags corresponds to an indication of a quality of therapy. According to one or more embodiments of this aspect, the determining the at least one characteristic of the at least one portion of the device in three dimensional space includes determining an orientation of the at least one portion of the device based at least in part on the interrogation.

According to one or more embodiments of this aspect, the determining of the at least one characteristic of the at least one portion of the device in three dimensional space includes determining a position of the treatment element of the device based at least in part on the interrogation. According to one or more embodiments of this aspect, the device further includes an elongated body of one of a rigid and compliant material having a proximal portion, a distal portion and a lumen extending between the proximal portion and the distal portion. The at least one wireless tag includes a plurality of wireless tags, respective wireless tags of the plurality of wireless tags is embedded within at least two selected from a group consisting of a shaft, tip, balloon and guidewire lumen of the device.

According to one or more embodiments of this aspect, the processing circuitry is further configured to determine an orientation between components of the device based at least in part on the interrogation. According to one or more embodiments of this aspect, the at least one treatment element of the device is expandable. The at least one wireless tag includes a plurality of wireless tags embedded within the expandable treatment element of the device where the interrogation of the plurality of wireless tags indicates at least one characteristic of expansion of one of an expandable and compliant treatment element of the device.

According to one or more embodiments of this aspect, the at least one characteristic of expansion of the expandable treatment element of the device includes a distance between wireless tags during expansion of the expandable portion of the device. According to one or more embodiments of this aspect, the causing of the at least one characteristic of the at least one portion of the device relative to the recipient to be visually indicated at least in part by overlaying the visual indication on a mapping of the recipient. According to one or more embodiments of this aspect, the mapping is a three dimensional mapping of the recipient.

According to one or more embodiments of this aspect, the causing of the at least one characteristic of the at least one portion of the device relative to the recipient to be indicated at least in part by at least one of a visual indication, audio indication and haptic indication associated with extended reality. According to one or more embodiments of this aspect, the interrogation includes receiving wireless data from the wireless tag, the wireless data including data selected from a group of temperature data, treatment element data, impedance data, pressure data, leak data and flow velocity data. According to one or more embodiments of this aspect, at least one interrogation device in communication with the tracking device, the interrogation device configured to perform the interrogating of the at least one wireless tag.

According to another aspect of the disclosure, a method for assessing at least one characteristic of a device within a recipient is provided. The device is removably insertable into the recipient where the device includes at least one of a treatment element and implant, and at least one wireless tag positioned within at least one portion of the device. If the device is inserted into the recipient, the at least one wireless tag positioned within at least one portion of the device is interrogated. At least one characteristic of at least one portion of the device in three dimensional space is determined based at least in part on the interrogation of the at least one wireless tag. The at least one characteristic of the at least one portion of the device relative to the recipient is caused to be indicated.

According to one or more embodiments of this aspect, determining at least one of an impedance quantity and distance between wireless tags by assessing a signal strength and response time is determined. According to one or more embodiments of this aspect, the impedance quantity between the wireless tags corresponds to an indication of a quality of therapy.

According to one or more embodiments of this aspect, the determining the at least one characteristic of the at least one portion of the device in three dimensional space includes determining an orientation of the at least one portion of the device based at least in part on the interrogation. According to one or more embodiments of this aspect, the determining of the at least one characteristic of the at least one portion of the device in three dimensional space includes determining a position of the treatment element of the device based at least in part on the interrogation.

According to one or more embodiments of this aspect, the device further includes an elongated body of one of a rigid and compliant material having a proximal portion, a distal portion and a lumen extending between the proximal portion and the distal portion. The at least one wireless tag includes a plurality of wireless tags, respective wireless tags of the plurality of wireless tags being embedded within at least two selected from a group consisting of a shaft, tip, balloon and guidewire lumen of the device. According to one or more embodiments of this aspect, determining an orientation between components of the device is determined based at least in part on the interrogation.

According to one or more embodiments of this aspect, the at least one treatment element of the device is expandable. The at least one wireless tag includes a plurality of wireless tags embedded within the expandable treatment element of the device where the interrogation of the plurality of wireless tags indicates at least one characteristic of expansion of one of an expandable and compliant treatment element of the device. According to one or more embodiments of this aspect, the at least one characteristic of expansion of the expandable treatment element of the device includes a distance between wireless tags during expansion of the expandable portion of the device.

According to one or more embodiments of this aspect, the causing of the at least one characteristic of the at least one portion of the device relative to the recipient to be visually indicated at least in part by overlaying the visual indication on a mapping of the recipient. According to one or more embodiments of this aspect, the mapping is a three dimensional mapping of the recipient. According to one or more embodiments of this aspect, the causing of the at least one characteristic of the at least one portion of the device relative to the recipient to be indicated at least in part by at least one of a visual indication, audio indication and haptic indication associated with extended reality.

According to one or more embodiments of this aspect, the interrogation includes receiving wireless data from the wireless tag, the wireless data including data selected from a group of temperature data, treatment element data, impedance data, pressure data, leak data and flow velocity data. According to one or more embodiments of this aspect, at least one interrogation device is in communication with the tracking device, the interrogation device configured to perform the interrogating of the at least one wireless tag.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

One or more characteristics of a device relative to a recipient (e.g., a person receiving treatment and/or a procedure) can impact the quality and efficacy of medical treatment. For example, appropriate positioning of the catheter for both ablations at the pulmonary vein (PVI) as well as ablations at other anatomical structures (PVI+) significantly impacts lesion quality and therapy efficacy. The instant disclosure at least in part solves at least one problem with existing system by providing a method and system for determining at least one characteristic of a device relative to a recipient such as position, location and/or orientation of the device.

Before describing in detail exemplary embodiments, it is noted that the embodiments reside primarily in combinations of apparatus components and processing steps related to determining at least one characteristic of a device relative to a recipient such as position, location and/or orientation of the device. Accordingly, components have been represented where appropriate by conventional symbols in the drawings, showing only those specific details that are pertinent to understanding the embodiments so as not to obscure the disclosure with details that will be readily apparent to those of ordinary skill in the art having the benefit of the description herein. Like numbers refer to like elements throughout the description.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 1:
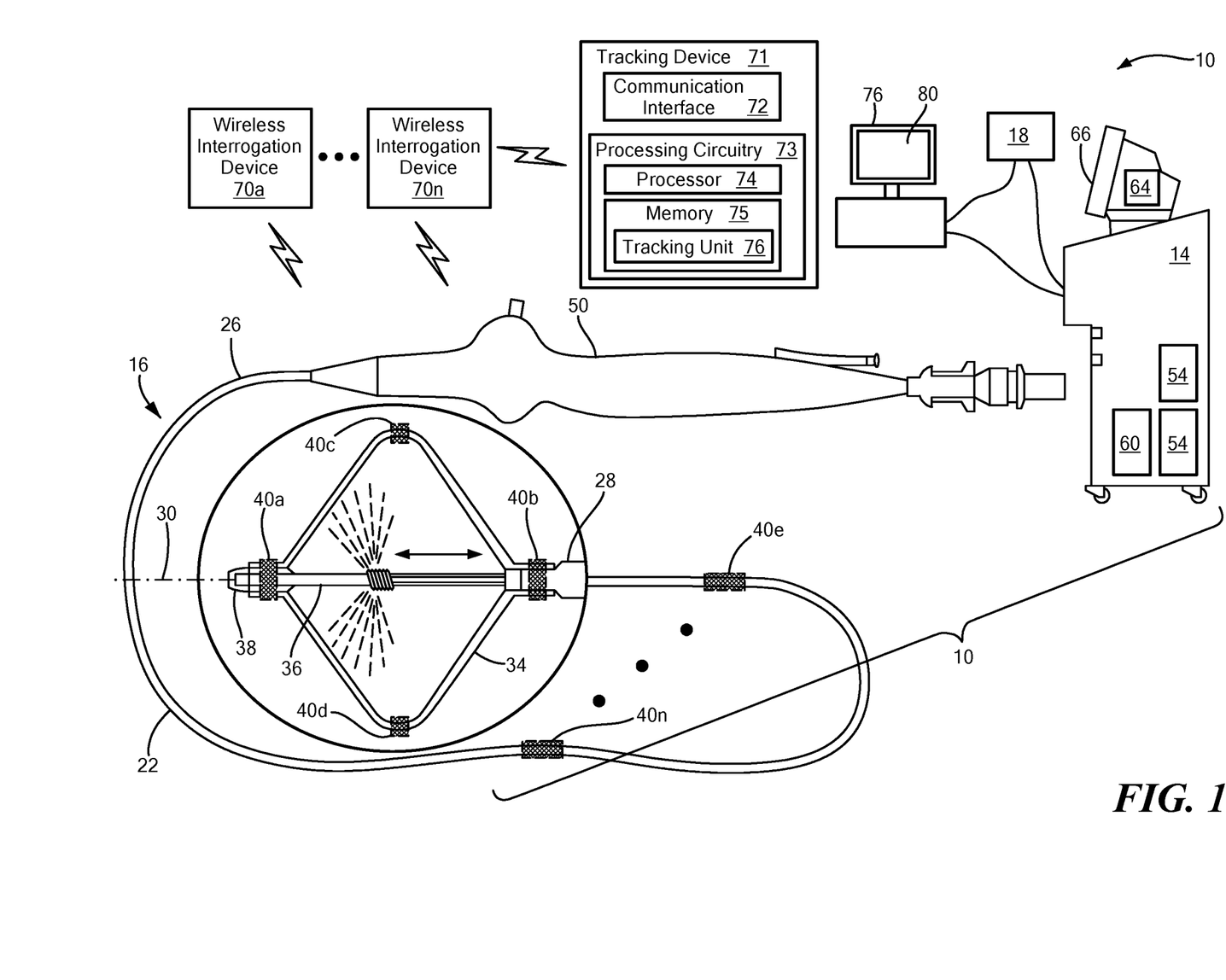
FIG. 1 is a diagram of an example of a system in accordance with the principles of the invention.
Figure 2:
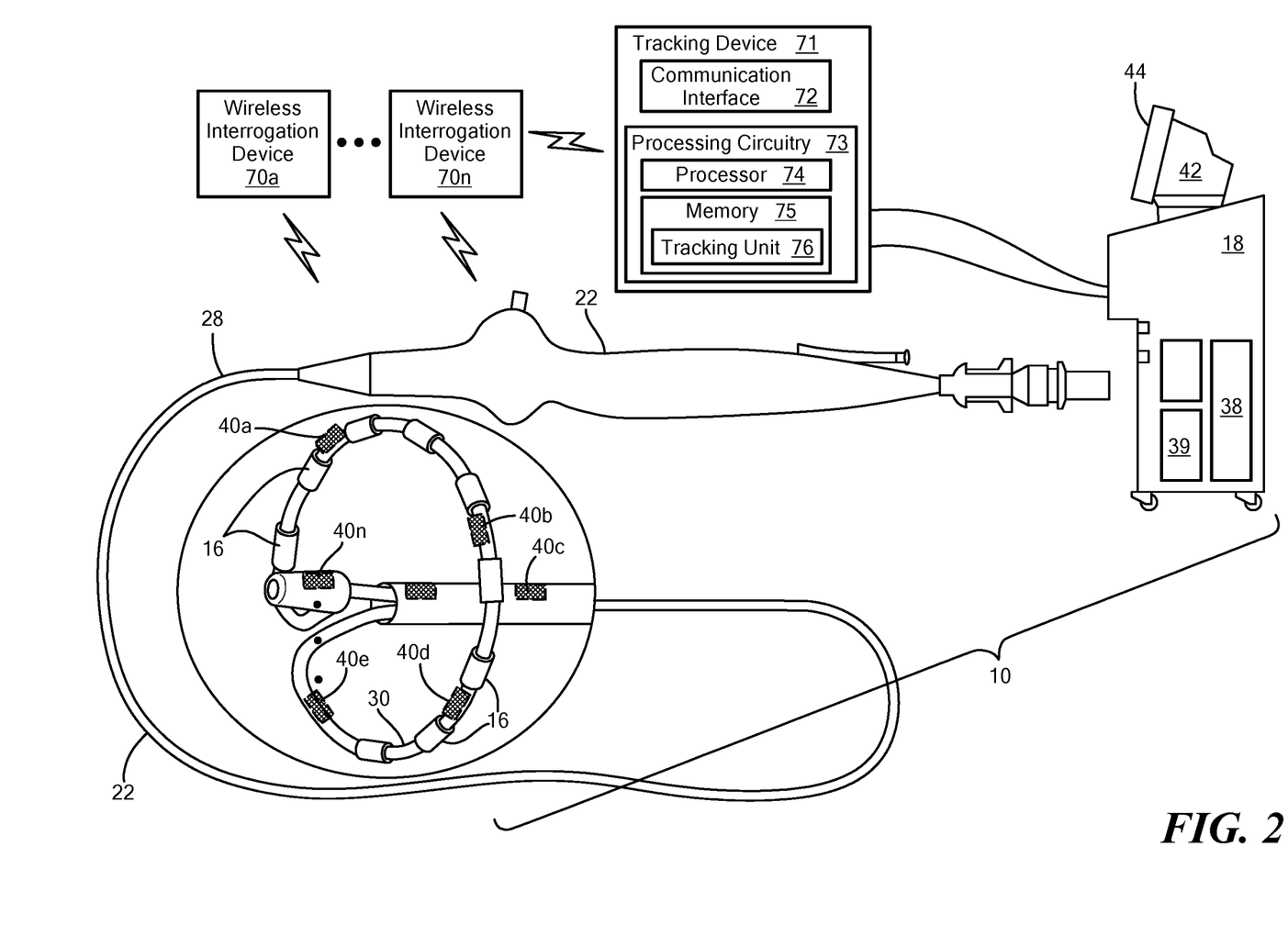
FIG. 2 is a diagram of another example the system in accordance with the principles of the invention.

Referring now to the drawing figures in which like reference designations refer to like elements, an embodiment of a medical system constructed in accordance with the principles of the present invention is shown in FIGS. 1 and 2, generally designated as "10." In its simplest form, the system 10 includes a navigation system 12, although the system 10 may also include a control unit 14 or operating console and a device 16 in communication with the navigation system 12 and the control unit 14. The system 10 may further include an imaging system 18 for obtaining images of anatomical features within a recipient.

The device 16 may be a treatment and/or therapy delivery device. The device 16 may include an elongate body 22 of rigid or compliant material passable through a recipient's vasculature and/or proximate to a tissue region for diagnosis or treatment. For example, the device 16 may be a catheter that is deliverable to the tissue region via a sheath or intravascular introducer (not shown). The elongate body 22 may define a proximal portion 26, a distal portion 28, and a longitudinal axis 30, and may further include one or more lumens disposed within the elongate body 22 thereby providing mechanical, electrical, and/or fluid communication between the elongate body proximal portion 26 and the elongate distal portion 28. In one or more embodiments, the device 16 may be comprised of at least one of polymer(s), metal(s), tissue and a living substrate.

The device 16 may further include one or more treatment elements 34 (i.e., treatment portions of device 16) at, coupled to, or on the elongate body distal portion 28 for energetic, therapeutic, and/or investigatory interaction between the device 16 and a treatment site or region. The treatment region element(s) 34 may deliver, for example, cryogenic therapy, radiofrequency (e.g., pulsed radio frequency (pRF), pulsed field ablation (PFA), etc.) energy, ultrasound energy, laser energy, or other energetic transfer with a tissue area in proximity to the treatment element(s), including cardiac tissue, and/or biological and/or drug therapies such as gene, cell and tissue construct therapies. For example, the treatment element(s) 34 may include thermally transmissive regions in thermal communication with a coolant or heat source, thermally transmissive regions in electrical communication with a power source, surface therapeutic elements such as surface radiofrequency electrodes, or the like. While the embodiments described herein may be through vessels, the disclosure is equally applicable to MIS and/or percutaneously performed treatments like Transcatheter Mitral Valve Repair Additionally, the device 16 may include more than one type of treatment element 34. In the exemplary system shown in FIG. 1, the device 16 may include a treatment element 34 that is expandable, such as one or more balloons. The expandable treatment element 34 may be coupled to a portion of the elongate body distal portion 28. The device 16 may optionally include a shaft 36 that includes a guidewire lumen and is slidably disposed within the elongate body 22 and at least a portion of the shaft 36 may be located within the expandable treatment element 34. The shaft 36 may further include or define a distal tip 38 that may protrude beyond the distal end of the expandable treatment element 34, and which may define an aperture in communication with the guidewire lumen. The expandable treatment element 34 may further include one or more material layers providing for puncture resistance, radiopacity, or the like. If the device 16 is used to delivery cryotherapy (or if used with another energy modality that requires fluid to be delivered to the inner chamber of the treatment element 34), the device may also include one or more fluid injection elements. The device 16 may also include one or more treatment elements in communication with a power source, such as one or more electrodes in communication with a source or radiofrequency energy.

Alternatively, the device 16 may include one or more treatment elements that are not expandable. For example, the device 16 may be a focal catheter that includes one or more electrodes on the distal portion, or may be a device that includes at least one carrier arm bearing one or more treatment electrodes 34 (as shown in the exemplary system of FIG. 2). Each treatment electrode 34 may be considered to be a treatment element. A device having a non-expandable treatment element may also include one or more fluid injection elements within the elongate body proximate the one or more treatment elements (for example, treatment electrode(s)). The device 16 shown in FIG. 2 may include one or more carrier arms 44 that are coupled to a shaft 46 and are transitionable between a first configuration in with each carrier arm 44 is in an at least substantially linear configuration and a second configuration in which each carrier arm 44 is in an expanded configuration.

Although not shown, the system 10 may include one or more sensors to monitor the operating parameters throughout the system, including for example, pressure, temperature, flow rates, volume, power delivery, impedance, or the like in the control unit 14 and/or the device 16, in addition to monitoring, recording or otherwise conveying measurements or conditions within the device 16 or the ambient environment at the distal portion of the device 16. The sensor(s) may be in communication with the control unit 14 for initiating or triggering one or more alerts or therapeutic delivery modifications during operation of the device 16. One or more valves, controllers, or the like may be in communication with the sensor(s) to provide for the controlled dispersion or circulation of fluid through the lumens/fluid paths of the device 16. Such valves, controllers, or the like may be located in a portion of the device 16 and/or in the control unit 14.

The device 16 may include a handle 50 coupled to the elongate body proximal portion 26. The handle 50 may include circuitry for identification and/or use in controlling of the device 16 or another component of the system. Additionally, the handle 50 may also include connectors that are mateable to the control unit 14 to establish communication between the device 16 and one or more components or portions of the control unit 14. The handle 50 may also include one or more actuation or control features that allow a user to control, deflect, steer, or otherwise manipulate a distal portion of the device 16 from the proximal portion of the device 16. For example, the handle 50 may include one or more components such as a lever or knob for manipulating the elongate body 22 and/or additional components of the device 16.

As used herein, the term "control unit 14" for simplicity may include any system components that are not part of the device 16 itself, other than components of the navigation system 12 and the imaging system 18, regardless of whether the component is physically located within or external to the control unit 14. Further, the navigation system 12 may be a standalone system in communication with the control unit 14 or may be contained within or integrated with the control unit 14, even though it is shown as being physically separated from the control unit in FIGS. 1 and 2. The control unit 14 may include one or more components for the delivery of one or more energy modalities for which the system is used. For example, if the system 10 is used to deliver cryotherapy, the control unit 14 may include a supply 54 of a fluid such as a coolant, cryogenic refrigerant, or the like, an exhaust or scavenging system for recovering or venting expended fluid for re-use or disposal, as well as various control mechanisms. In addition to providing an exhaust function for the fluid or coolant supply 54, the control unit 14 may also include pumps, valves, controllers or the like to recover and/or re-circulate fluid delivered to the handle 50, the elongate body 20, and/or the fluid pathways of the device 16. Further, a vacuum pump 56 in the control unit 14 may create a low-pressure environment in one or more conduits within the device 16 so that fluid is drawn into the conduit(s)/lumen(s) of the elongate body 22, away from the distal portion 28 and towards the proximal portion 26 of the elongate body 22. Additionally or alternatively, the control unit 14 may include an energy source 60 as a treatment or diagnostic mechanism in communication with the treatment element(s) 34 of the device 16. The energy source 60 may be a radiofrequency generator having a plurality of output channels, with each channel coupled to an individual treatment electrode 34. The radiofrequency generator 60 may be operable in one or more modes of operation.

The control unit 14 may include one or more controllers, processors, and/or software modules containing processing circuitry configured to execute instructions or algorithms to provide for the automated operation and performance of the features, sequences, calculations, or procedures described herein and/or required for a given medical procedure. Further, the control unit 14 may include one or more user input devices, controllers, and displays 66 for collecting and conveying information from and to the user.

As a non-limiting example, the navigation system 12 may be in communication with a plurality of wireless interrogation devices 70*a-n* (hereinafter referred to as interrogation device 70), and may include tracking device 71. Tracking device 71 may include communication interface 72 for communicating with one or more entities in system 10 such as with wireless interrogation device 70 and/or imaging system 18, etc. Tracking device 71 includes processing circuitry 73. The processing circuitry 73 may include a processor 74 and memory 75. In particular, in addition to or instead of a processor, such as a central processing unit, and memory, the processing circuitry 73 may comprise integrated circuitry for processing and/or control, e.g., one or more processors and/or processor cores and/or FPGAs (Field Programmable Gate Array) and/or ASICs (Application Specific Integrated Circuitry) adapted to execute instructions. The processor 74 may be configured to access (e.g., write to and/or read from) memory 75, which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory).

Thus, the tracking device 71 further has software stored internally in, for example, memory 75, or stored in external memory (e.g., database, storage array, storage device, etc.) accessible by the tracking device 71 via an external connection. The software may be executable by the processing circuitry 73. The processing circuitry 73 may be configured to control any of the methods and/or processes described herein and/or to cause such methods, and/or processes to be performed, e.g., by tracking device 71. Processor 74 corresponds to one or more processors 74 for performing tracking device 71 functions described herein. The memory 75 is configured to store data, programmatic software code and/or other information described herein. In some embodiments, the software may include instructions that, when executed by the processor 74 and/or processing circuitry 73, causes the processor 74 and/or processing circuitry 73 to perform the processes described herein with respect to tracking device 71. For example, processing circuitry 73 of the tracking device 71 may include tracking unit 76 configured to perform one or more functions such as to determine one or more characteristics of the device 16 relative to the recipient, for example, as described herein.

In one or more embodiments, tracking device 71 collects and processes signals from one or more wireless interrogation devices 70, and a display 77 that displays to the user the one or more characteristics of the device 16 within the recipient's body 78 and/or relative to the target anatomical feature (for example, a pulmonary vein ostium), recommended treatment areas, tissue thickness, or the like. In one or more embodiments, tracking device 71 is configured to communicate with one or more other monitoring devices such as cardiac monitors among other devices that may not be part of the therapy delivery. Additionally or alternatively, this information may be displayed on the display 66 of the control unit 14. Further, the tracking device 71 may execute software and display a software interface 80 with which the user may interact to make a selection, rotate and flag an image, open folders, control the navigation system 12, or the like. As a non-limiting example, the user may interact with the software interface 80 using a touch screen, a keyboard, a mouse, or other input device.

It will be understood that although the navigation tracking device 71 is disclosed herein as performing one or more functions discussed herein, it will be understood that these one or more functions may additionally or alternatively be performed by one or more processors 64 within the control unit 14.

The navigation system 12 may be in communication with one or more of wireless interrogation devices 70a-70n (hereinafter collectively referred to as interrogation device 70), and may include a reference wireless tag(s) (not shown), and a processing unit that collects and processes signals from the wireless tags 40a-40n (hereinafter collectively referred to as wireless tag 40), and a display 80 that displays to the user the location of the device 16 within the recipient's body 78 and/or relative to the target anatomical feature (for example, a pulmonary vein ostium), recommended treatment areas, tissue thickness, or the like. In one or more embodiments, one or more wireless tags 40 may be one or more of semi-passive tags, passive tags, etc. For example, one or more wireless tags 40 may be wired within and/or with device 16 but may communicate wirelessly while one or more other wireless tags 40 may not be wired. Additionally or alternatively, this information may be displayed on the display 66 of the control unit 14. Alternatively, the navigation system 12 may be in communication with the control unit energy source 60. For example, processing circuitry 73 may be configured, programmed, or programmable to perform the calculations and make the determinations discussed in greater detail below to identify a location of the device 16 relative to a target location for the device 16. Further, processing circuitry 73 may execute software and display a software interface 80 with which the user may interact to make a selection, rotate and flag an image, open folders, control the navigation system 12, or the like. As a non-limiting example, the user may interact with the software interface 80 using a touch screen, a keyboard, a mouse, or other input device.

It will be understood that although the processing circuitry 73 is disclosed herein as performing the calculations discussed herein, it will be understood that the calculations may additionally or alternatively be performed by one or more processors 64 within the control unit 14.

As shown in FIGS. 1 and 2, the one or more interrogation devices 70 may be positioned at one or more positions relative to a recipient where the one or more interrogation devices 70 interrogate one or more wireless tags 40 positioned on and/or embedded within one or more portions of device 16. In one or more embodiments, the wireless tags 40 may be positioned on and/or embedded within one or more portions of device 16 along an axis or curve of the device. In one or more embodiments, the wireless tags 40 may be positioned on and/or embedded within one or more portions of device 16 along an axis, plane or curve of the device 16. In one or more embodiments, the wireless tags 40 may be positioned on and/or embedded within one or more portions of device 16 in non-uniform shapes of the device 16 and/or radially extending asymmetrically around the device 16 such as the circumference of a balloon, catheter, implant, etc., i.e., in a non-circular configuration, and in one or more planes. In one or more embodiments, tracking device 71 is configured to calculate one or more characteristics of the device 16 relative to the recipient based on the one or more wireless signals received from one or more wireless tags 40 by one or more interrogation devices 70. In one or more embodiments, the characteristics may include one or more of position of one or more portions of device 16 relative to recipient, orientation of one or more portions of device 16 relative to recipient, among other characteristics of device 16 that are determinable based at least in part on signals received from wireless tags 40. In one or more embodiments, the one or more characteristics are based at least in part on the wireless signal powers of the wireless signals received from wireless tags 40, as described herein. For example, at least two interrogation devices 70 may receive a wireless signal from the same wireless tag 40 but at a different power level due to, for example, the distance of each interrogation relative to the wireless tag 40. Therefore, the power levels may be used, in one or more embodiments, to determine the position of the wireless tag 40 relative to two interrogation devices 70, whose position(s) relative to the recipient may be predefined and/or determined using a similar process where one or more wireless tags 40 are removably affixed to one or more portions of the recipient such that the position and/or orientation of the recipient can be determined. The processing circuitry 73 may perform one or more of these calculations many times during a procedure, frequently updating the characteristic(s) of the device 16 and/or the recipient and displaying such to the user so the user can visualize the location of the device 16 relative to the recipient in real time.

In one or more embodiments, the device 16 may be a catheter such that one or more wireless tags 40 can be embedded in/on one or more of the catheter shaft, balloon, guidewire lumen/tip and/or handle of the Achieve, Cryoballoon or Sheath, there allowing real-time tracking of the catheter's geometry. However, device 16 is not limited to catheters. In one or more embodiments, one or more wireless tags 40 are non-blood contacting components of system 10 such that wireless tags 40 do not contact blood and/or fluids of the recipient at least during the medical procedure. In one or more embodiments, one or more interrogation devices 70 are located outside of the recipient where one or more of these interrogation devices 70 may include skin-contacting interrogation devices and/or non-skin contacting interrogation devices. In one or more embodiments, one or more wireless tags 40 may be independent of each other or form a rigid or compliant array such as a communication net or mesh network.

The imaging system 18 may be one or more known systems suitable for creating images of locations within a recipient's body. For example, the imaging system may create images in Digital Imaging and Communications in Medicine (DICOM) format. The imaging system 18 may be in communication with and digitally transmit images to the navigation system 12 and/or the control unit 14 for further processing. Alternatively, images recorded by the imaging system 18 may be recorded and transferred to the navigation system 12 and/or the control unit 14 by a user.

Figure 3:
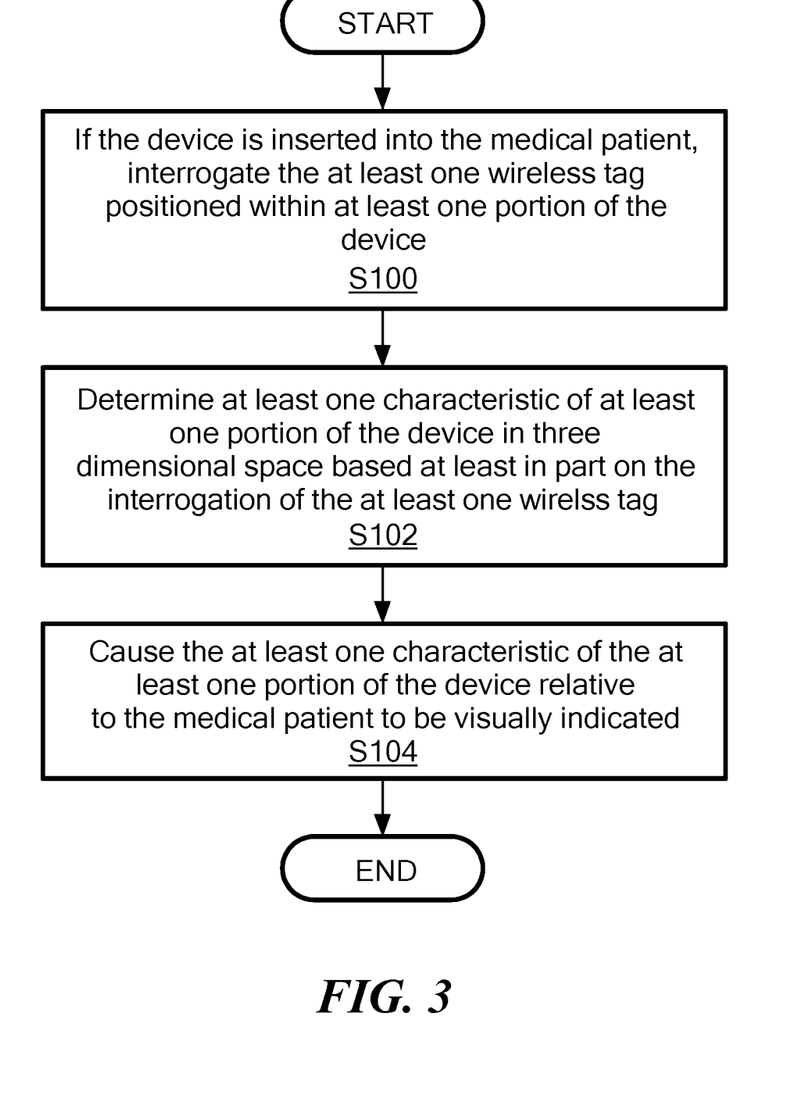
FIG. 3 is a flowchart of an example tracking process in accordance with the principles of the invention.

FIG. 3 is an exemplary tracking process according to one or more embodiments of the invention. One or more Blocks and/or functions performed by tracking device 71 may be performed by one or more elements of tracking device 71 such as by tracking unit 76 in processing circuitry 73, processor 74, radio interface communication interface 72, etc. In one or more embodiments, tracking device 71 such as via one or more of processing circuitry 73, processor 74 and communication interface 72 is configured to, if the device is inserted into the recipient, interrogate (Block S100) at least one wireless tag 40 positioned within the at least one portion of the device 16, as described herein. In one or more embodiments, tracking device 71 such as via one or more of processing circuitry 73, processor 74 and communication interface 72 is configured to determine (Block S102) at least one characteristic of the at least one portion of the device 16 in three dimensional space based at least in part on the interrogation of the at least one wireless tag 40, as described herein. In one or more embodiments, tracking device 71 such as via one or more of processing circuitry 73, processor 74 and communication interface 72 is configured to cause (Block S104) the at least one characteristic of the at least one portion of the device 16 relative to the recipient to be visually indicated, as described herein.

In one or more embodiments, wherein the processing circuitry 73 is further configured to determine information associated with one or more wireless tags 40 such as an impedance quantity or distance between wireless tags 40, spatial information, among other sensor data. In one or more embodiments, the impedance quantity between the wireless tags 40 corresponds to an indication of a quality (i.e., impedance quality) of therapy such as a quality of occlusion. In one or more embodiments, the impedance quality between wireless tags 40 may be determined by assessing one or more characteristics of transmissions between the wireless tags 40. In one or more embodiments, the one or more characteristics may include one or more of signal quality, strength and/or communication time, one or more of which may be affected by the types of medium (tissue, bone, blood, etc.) between the wireless tags 40. In one or more embodiments, changes one or more characteristics of the transmissions during navigation is caused by changing anatomy as the device moves. In one or more embodiments, spatial mapping of wireless devices 40 and/or inter-tag signal(s) are used to determine at least one characteristic of at least one portion of the device 16, therapy, and/or environment.

In one or more embodiments, the determining of the at least one characteristic of the at least one portion of the device 16 in three dimensional space includes determining an orientation of the at least one portion of the device 16 based at least in part on the interrogation. In one or more embodiments, the determining of the at least one characteristic of the at least one portion of the device 16 in three dimensional space includes determining a position of the treatment element of the device 16 based at least in part on the interrogation.

In one or more embodiments, the device 16 further includes an elongated body of a rigid or compliant material having a proximal portion, a distal portion and a lumen extending between the proximal portion and the distal portion and may be comprised of polymer, metal, tissue, and/or a living substrate. The at least one wireless tag 40 includes a plurality of wireless tags 40, where respective wireless tags 40 of the plurality of wireless tags 40 are embedded within at least two selected from a group consisting of a shaft, tip, balloon and guidewire lumen of device 16. In one or more embodiments, the processing circuitry 73 is further configured to determine the position and contour of the device 16 based at least in part on the interrogation. In one or more embodiments, the at least one treatment element of the device 16 is expandable. The at least one wireless tag 40 includes a plurality of wireless tags 40 embedded within the expandable treatment element of the device 16 where the interrogation of the plurality of wireless tags 40 indicates at least one characteristic of expansion of the expandable treatment element of the device 16.

According to one or more embodiments, the processing circuitry 73 is further configured to determine an orientation between components of the device 16 based at least in part on the interrogation. According to one or more embodiments, the causing of the at least one characteristic of the at least one portion of the device relative to the recipient to be indicated at least in part by at least one of a visual indication, audio indication and haptic indication associated with extended reality. According to one or more embodiments, the interrogation includes receiving wireless data from the wireless tag 40, the wireless data including data selected from a group of temperature data, treatment element data, impedance data, pressure data, leak data and flow velocity data.

In one or more embodiments, the at least one characteristic of expansion of the expandable treatment element of the device 16 includes a distance between wireless tags 40 during expansion of the expandable portion of the device 16. In one or more embodiments, the causing of the at least one characteristic of the at least one portion of the device 16 relative to the recipient to be visually indicated includes overlaying the visual indication on a mapping of the recipient. In one or more embodiments, the mapping is a three dimensional mapping of the recipient. In one or more embodiments, the visual indication is provided by extended reality which may corresponds to mixed reality or an extension of augmented reality where interaction with the augmented environment may occur haptically and with data/decision making of the augmented environment. In one or more embodiments, the interrogation includes receiving wireless data from the wireless tag 40 where the wireless data including data selected from a group of temperature data and treatment element data. In one or more embodiments, the wireless tags 40 are radio frequency identification (RFID) wireless tags 40, although other short range technologies may be used such as near field communication (NFC) technology, for example.

Figure 4:
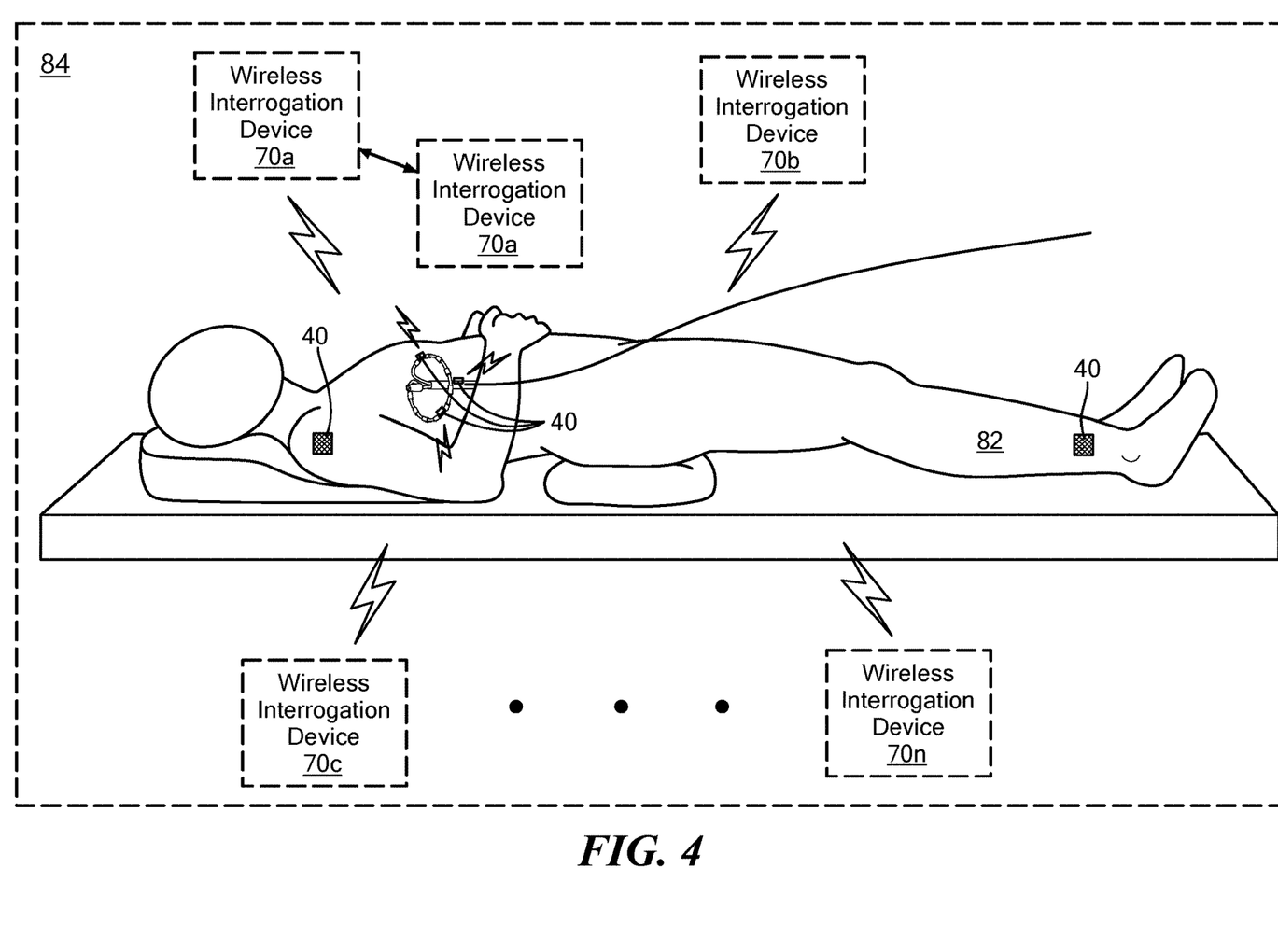
FIG. 4 is a diagram an example configuration of a portion of the system in accordance with the principles of the invention.
Figure 5:
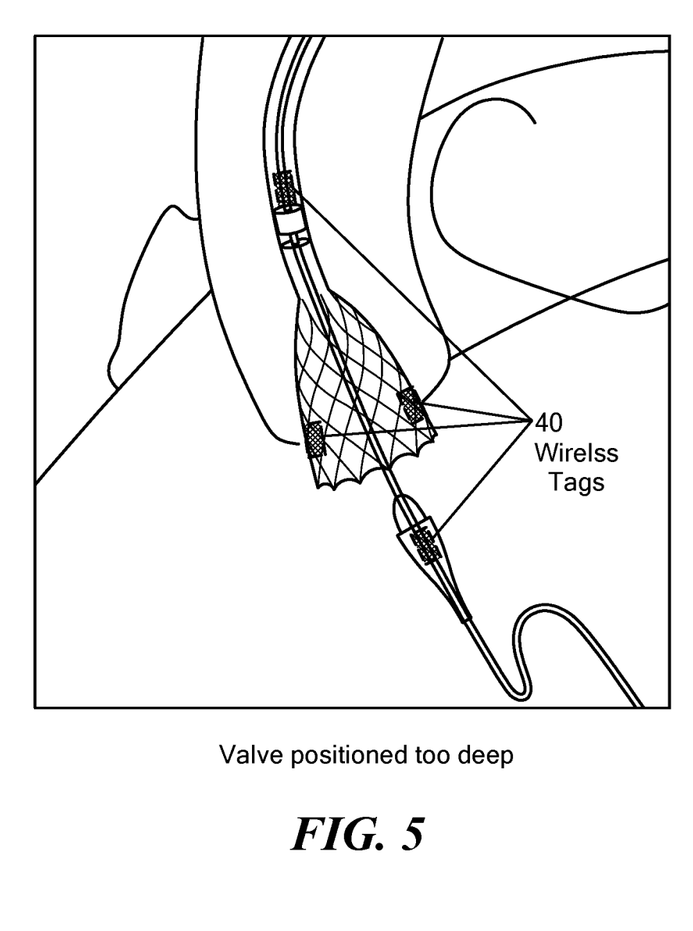
FIG. 5 is a graphical diagram of an instance of positioning of a medical device within a recipient in accordance with the principles of the invention.

FIG. 4 is a diagram of a portion of system 10 where one or more wireless tags 40 are used to tracking device 16 that has been removably inserted into recipient 82. In one or more embodiments, one or more of interrogation devices 70a-70n are at least temporarily positioned in and/or proximate environment 84. In one or more embodiments, at least one interrogation device 70 such as interrogation device 70 in this example may be repositionable within environment 84. Repositioning of at least one interrogation device 70 may help improve the accuracy of the determination of the characteristic(s) of the device 16. In one or more embodiments, one or more wireless tags 40 removably positioned on recipient 82 such that interrogation device 70 also determines one or more characteristics of one or more portions of the recipient. For example, one or more wireless tags 40 may be removably positioned at various locations on recipient 82 such as the recipient's leg, shoulder, etc., thereby allowing processing circuitry 73 to determine characteristics of device 16 relative to the interrogation devices 70 and to the wireless tags 40 positioned on recipient 82.

In one or more examples, two or more wireless tags 40 are positioned on recipient 82 proximate one or more treatment point and/or area(s) such that one or more characteristics of the device 16 relative to the treatment point and/or area are determined. For example, one or more wireless device 40 may be positioned on a recipient on one or more imaginary planes and/or one or more imaginary axes where the treatment point and/or a portion of the treatment area is located, thereby allowing for the determine of, for example, the position of the device 16 relative to the treatment point/area. In one or more examples, the treatment point is positioned at the origin and/or intersection of the x, y and z imaginary planes, such that planes one or more wireless tags 40 on the recipient for each of the imaginary planes allows processing circuitry 73 to determine, for example, the position of device relative to the treatment point. In one example, respective wireless tags 40 may be positioned at respective treatment points or target points. In one or more embodiments, determination of one or more characteristics of the device 16 may be based at least in part on the interrogation of wireless tags 40 embedded within the device 16 and positioned on the recipient 82. In one or more examples, processing circuitry 73 may be positioned on a vest such as a multi-electrode vest to help ensure the relative location of the wireless tags 40 with respect to anatomy.

Further, the location of one or more wireless tags 40 may be determined using a plurality of non-coplanar RFID readers in predetermined locations. The distances between each reader and the wireless tag 40 may be determined where these distances are then used to determine the location of the wireless tag 40 in three dimensional space at the time of the response.

FIGS. 5-8 are various diagrams of one or more wireless tags 40 embedded within and/or positioned on device 16 during various possible instances of a medical procedure according to one or more embodiments of the invention. For example, in FIG. 5 the valve is positioned too deep, where the valve position (e.g., an example of one characteristic of the device 16) is determined to be too deep based on the interrogation of one or more wireless tags 40. In particular, in one or more embodiments, the distance between one or more wireless tags 40 on one or more portions of device 16 are determinable by processing circuitry 73 based at least in part on the interrogation, thereby allowing processing circuitry 73 to determine the distance between one or more portions of device 16.

In one or more embodiments, one or more wireless tags 40 may be configured to transmit wireless data such as temperature data, treatment data, etc. For example, the one or more wireless tags 40 may be in communication with one or more sensors (not shown) in device 16 and/or positioned on recipient 82, and may report these measurements from the sensors to interrogation devices 70. In one or more embodiments, one or more wireless tags 40 may include one or more of these sensors. In one or more embodiments, strain and stress can be determined based at least in part on the known distance to a reader and/or other wireless device 40, and type of material. The strain and/or stress information can be combined with other information such as piezo data and/or FEA for decision making.

In one or more embodiments, one or more wireless tags 40 are passive, semi-passive and/or active wireless tags 40. For example, a passive wireless tag 40 may correspond to a wireless tag 40 where an interrogation signal from interrogation device 70 triggers the passive wireless tag to activated and transmit a wireless signal. In another example, semi-passive wireless tag 40 corresponds to a wireless tag 40 that uses an internal power source to turn on, which can be at least temporally charged from the radio frequency (RF) energy of the interrogation signal from the interrogation device 70. In another example, an active wireless tag 40 corresponds to a wireless tag 40 that has its own transmitter and power source such as a battery, i.e., a wireless tag 40 does not rely on interrogation signals from interrogation device 70 for power.

In one or more embodiments, processing circuitry 73 determines information associated with one or more wireless tags 40 such as an impedance between at least two wireless tags 40 where the impedance between wireless tags 40 is an indication of a quality of therapy such as a quality of occlusion. In one or more embodiments, the information associated with one or more wireless tags 40 includes spatial information associated with the wireless tags 40 and/or other sensor data. In one or more embodiments, the RF frequency of one or more wireless tags 40 may be in the high frequency range (3-30 MHz) and/or ultra-high frequency range (30 MHz+).

Figure 6:
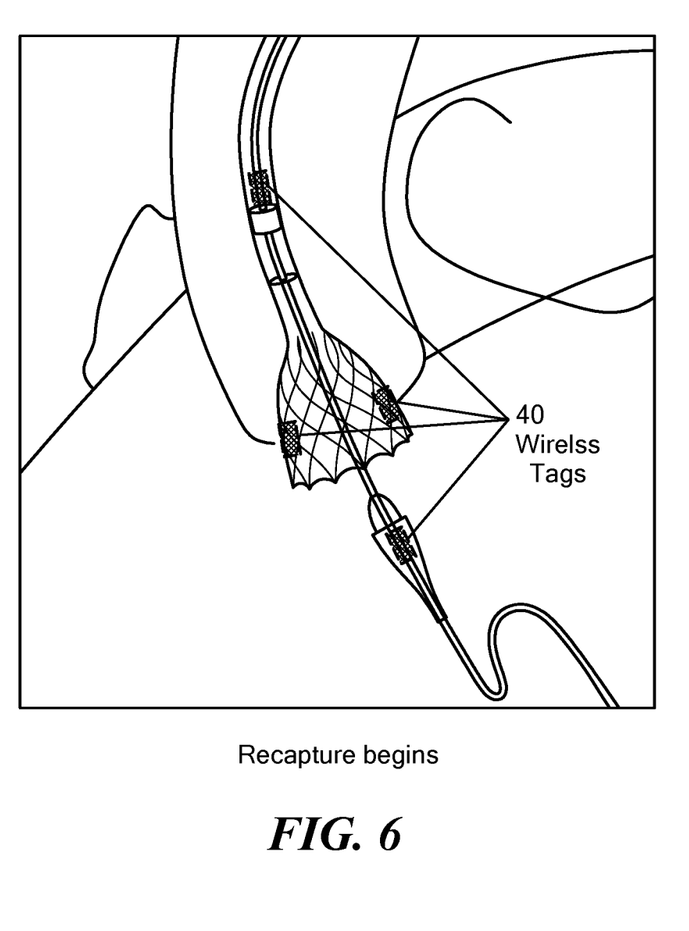
FIG. 6 is a graphical diagram of another instance of positioning of the medical device within a recipient in accordance with the principles of the invention.
Figure 7:
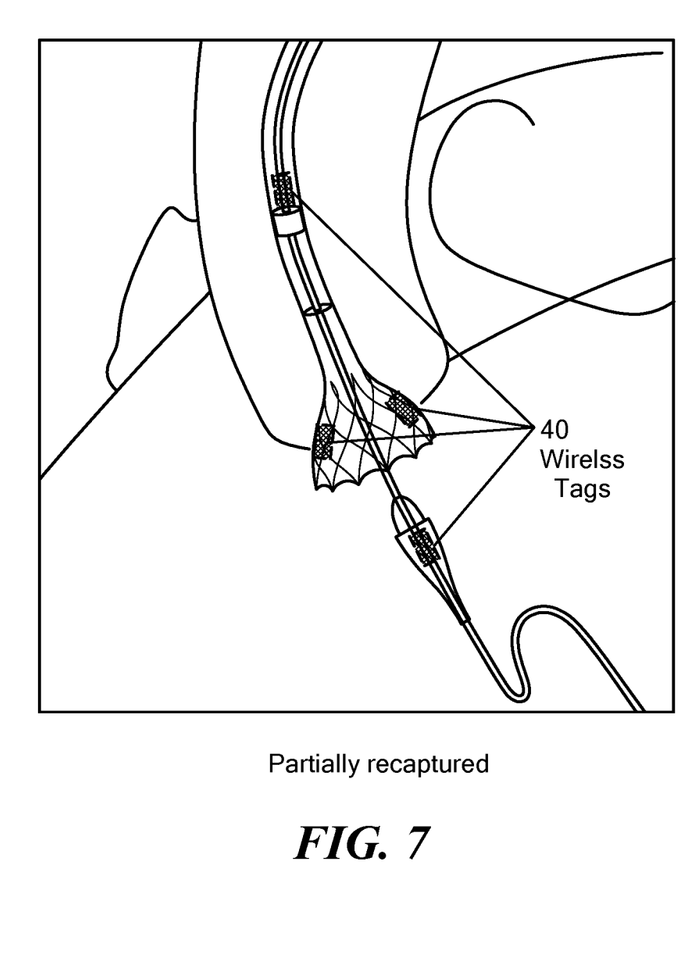
FIG. 7 is a graphical diagram of yet another instance of positioning of the medical device within a recipient in accordance with the principles of the invention.
Figure 8:
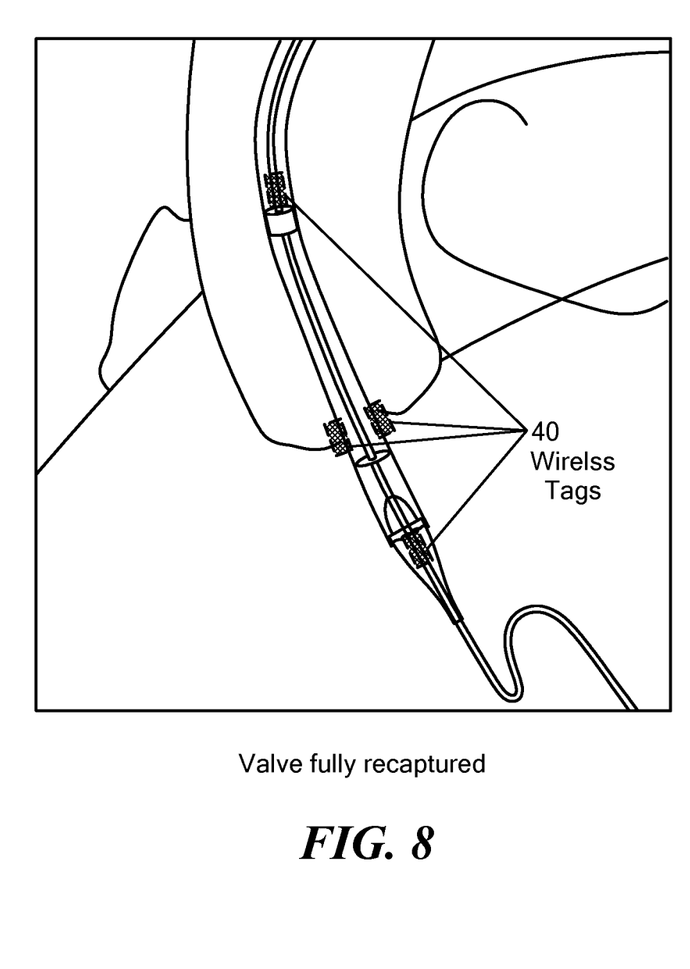
FIG. 8 is a graphical diagram of yet another instance of positioning of the medical device within a recipient in accordance with the principles of the invention.

FIG. 6 is a diagram of another instance of a medical procedure where the recapture of the valve begins and where one or more characteristics of the device 16 are determined based at least in part on the interrogation. FIG. 7 is a diagram of another instances of a medical procedure where the valve is at least partially recaptured and where one or more characteristics of the device 16 are determined based at least in part on the interrogation. FIG. 8 is a diagram of another instances of a medical procedure where the valve is fully recaptured and where one or more characteristics of the device 16 are determined based at least in part on the interrogation. In one or more embodiments described herein, the interrogation performed by interrogation devices 70 may be performed periodically, on demand and/or at the periodicity corresponding to the stage of the medical procedure (e.g., the interrogation frequency may be increased during the stages corresponding to FIGS. 7 and 8), for example.

Figure 9:
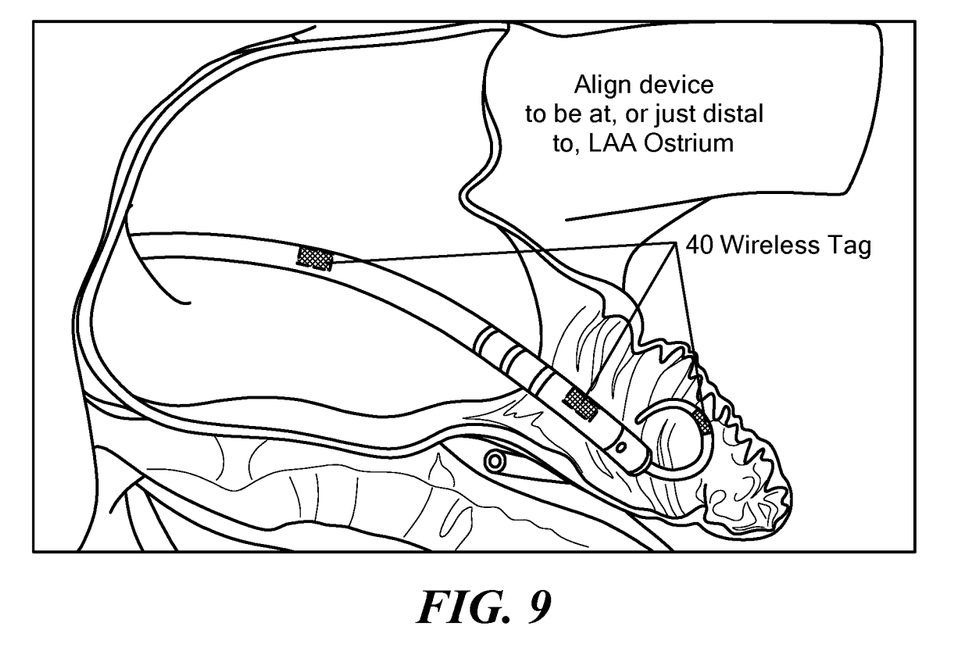
FIG. 9 is a graphical diagram of an instance of positioning of a medical device within a recipient in accordance with the principles of the invention.
Figure 10:
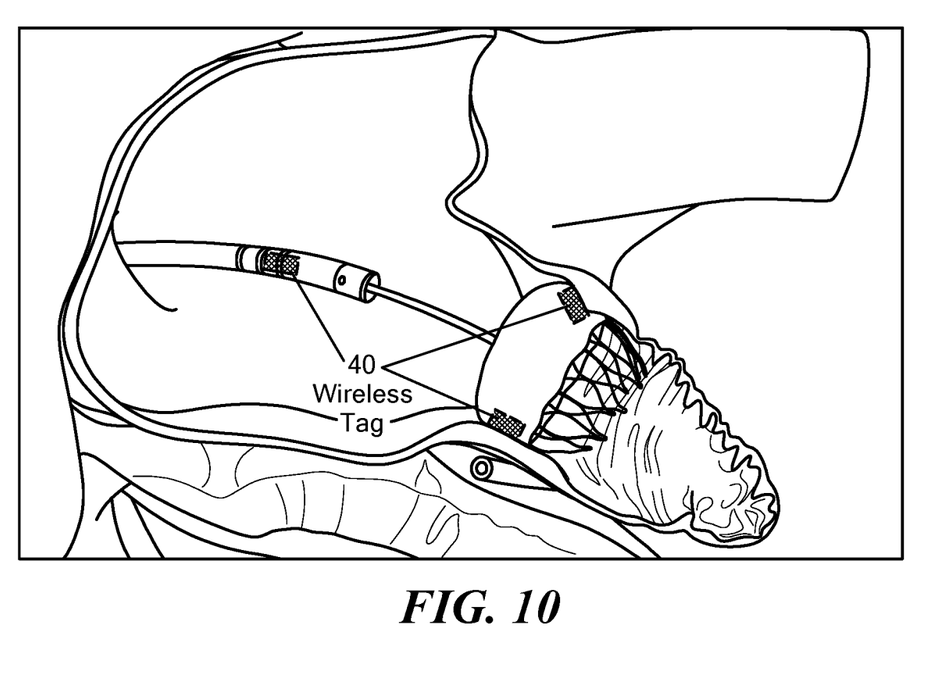
FIG. 10 is a graphical diagram of an instance of positioning of a medical device within a recipient in accordance with the principles of the invention.

FIGS. 9-10 is another example of various instances of another medical procedure where one or more characteristics of the device 16 are determined based at least in part on the interrogation. For example, device 16 is positioned at a treatment point based on the interrogation of various wireless tags 40 such as wireless tags 40 embedded within device 16 and positioned on the recipient, for example. Once the device 16 is determined to at least be in the correct position, the expandable element of the device 16 is expanded for treatment. In this example, wireless tags 40 are positioned at opposite sides/portions of the expandable element such as to allow processing circuitry 73 to determine one or more characteristics of the expandable portion of the device 16 such as a width and/or diameter of the expandable portion of the device 16, which may corresponds to a distance between wireless tags 40 embedded within the expandable portion of device 16. Further, one or more characteristics of the device 16 may include the trajectory of the device 16 and/or other motion related characteristics determinable by the change in position of one or more wireless tags 40 at least two interrogation instances.

Figure 11:
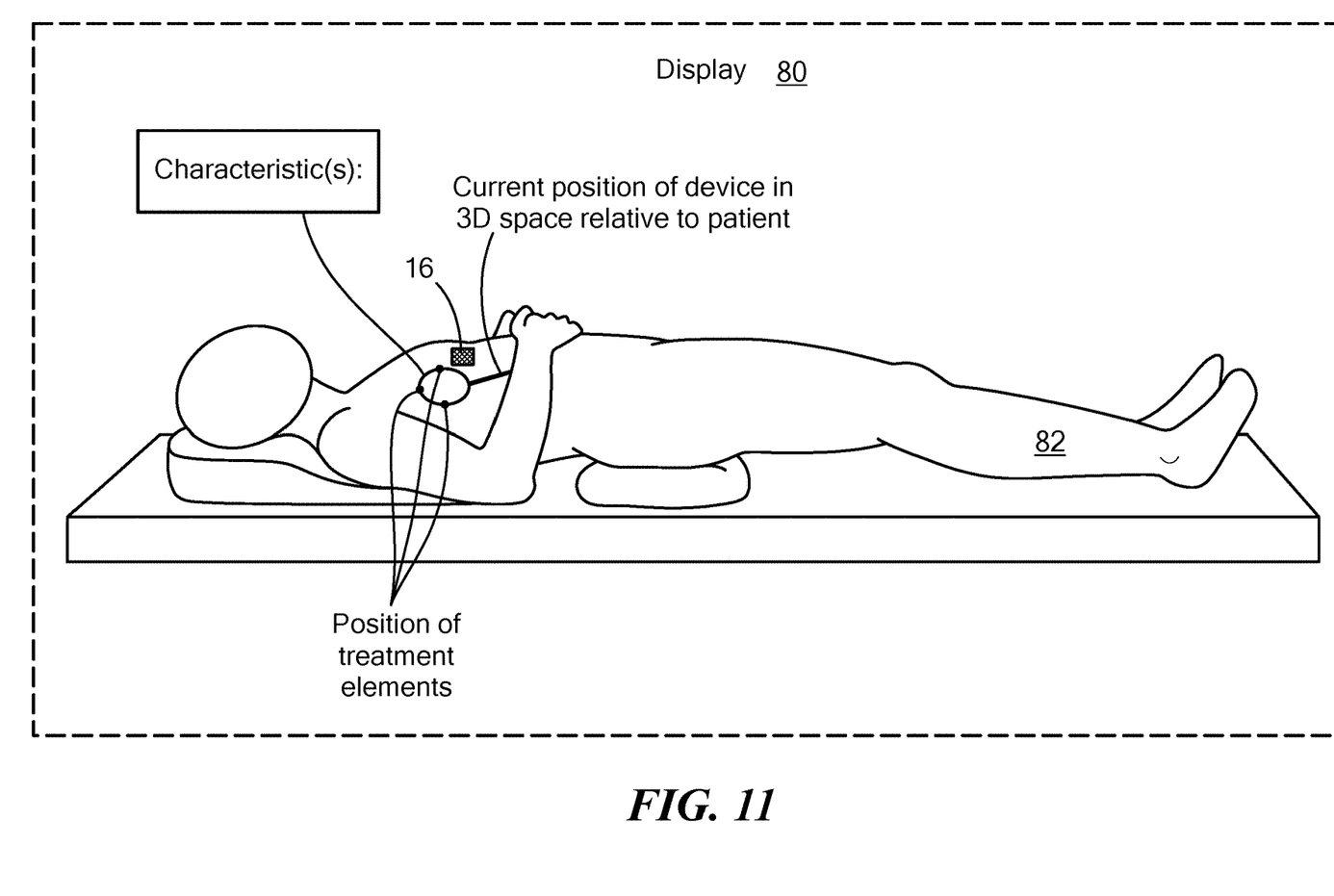
FIG. 11 is a diagram of an example visual indication on a display in accordance with the principles of the invention.

FIG. 11 is a diagram of an example visual indication based at least in part on the interrogation of one or more wireless tags 40. For example, display 80 may display one or more characteristics of the device 16 (e.g., expansion characteristics of expandable or compliant treatment element, and at least one of a physical, chemical, biological relationship with its immediate and/or predicated surroundings, etc.), treatment, and/or associated with the recipient 82 (e.g., repository, ECG, temperature of adjacent structures of/within the recipient 82). In one or more embodiments, the characteristics may include at least one of target PV, heart valve, infarct, proximity to an adjacent structure such as a phrenic nerve, esophagus, left bundle branch, etc., that may be visually indication. In one or more embodiments, the one or more characteristics may be indicated via at least one of a visual indication, audio indication and haptic indication using extended reality. In one or more embodiments, the visual indication may be provided by extended reality such as on a portable headset.

A broad range of minimally invasive procedures could benefit from having therapeutic products integrated with wireless navigation capabilities described herein. For example, the implant procedure of EVICD requires precise visualization of the anatomy and awareness of where anatomical structures are located relative to one another. Overlaying navigation of products with wireless tags 40 on a pre- or real-time acquired image significantly enhances procedure predictability and lowers recipient risk. This tracking can be integrated with an extended reality system in order for the physician to track without fluoro in real-time, so as to better address critical needs such as occlusion gaps and electrical reconnections.

As will be appreciated by one of skill in the art, the concepts described herein may be embodied as a method, data processing system, computer program product and/or computer storage media storing an executable computer program. Accordingly, the concepts described herein may take the form of an entirely hardware embodiment, an entirely software embodiment or an embodiment combining software and hardware aspects all generally referred to herein as a "circuit" or "module." Any process, step, action and/or functionality described herein may be performed by, and/or associated to, a corresponding module, which may be implemented in software and/or firmware and/or hardware. Furthermore, the disclosure may take the form of a computer program product on a tangible computer usable storage medium having computer program code embodied in the medium that can be executed by a computer. Any suitable tangible computer readable medium may be utilized including hard disks, CD-ROMs, electronic storage devices, optical storage devices, or magnetic storage devices.

Some embodiments are described herein with reference to flowchart illustrations and/or block diagrams of methods, systems and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer (to thereby create a special purpose computer), special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable memory or storage medium that can direct a computer or other programmable data processing apparatus to function in a particular manner, such that the instructions stored in the computer readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

It is to be understood that the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved. Although some of the diagrams include arrows on communication paths to show a primary direction of communication, it is to be understood that communication may occur in the opposite direction to the depicted arrows.

Computer program code for carrying out operations of the concepts described herein may be written in an object oriented programming language such as Java® or C++. However, the computer program code for carrying out operations of the disclosure may also be written in conventional procedural programming languages, such as the "C" programming language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the invention, which is limited only by the following claims.

What is claimed is:

1. A system for assessing at least one characteristic of a device within a recipient, the system comprising:
  a device removably insertable into the recipient, the device including a treatment element, the treatment element including a balloon and a plurality of electrodes configured to deliver pulsed field ablation energy and at least one wireless tag embedded on an outer surface of the balloon;
  a tracking device including processing circuitry configured to:
    when the device is inserted into the recipient, interrogate the at least one wireless tag, the interrogation of the at least one wireless tag indicating a distance between a plurality of the at least one wireless tag during expansion of the balloon;
    determine at least one characteristic of at least one portion of the device in three dimensional space based at least in part on the interrogation of the at least one wireless tag, the interrogation including receiving wireless data from the at least one wireless tag, the wireless data including treatment element data; and cause the at least one characteristic of the at least one portion of the device relative to the recipient to be indicated.

2. The system of claim 1, wherein the processing circuitry is further configured to determine at least one of an impedance quantity and distance between wireless tags by assessing a signal strength and response time.

3. The system of claim 2, wherein the impedance quantity between the wireless tags corresponds to an indication of a quality of therapy.

4. The system of claim 1, wherein the determining the at least one characteristic of the at least one portion of the device in three dimensional space includes determining an orientation of the at least one portion of the device based at least in part on the interrogation.

5. The system of claim 1, wherein the determining of the at least one characteristic of the at least one portion of the device in three dimensional space includes determining a position of the treatment element of the device based at least in part on the interrogation.

6. The system of claim 1, wherein the processing circuitry is further configured to determine an orientation between components of the device based at least in part on the interrogation.

7. The system of claim 1, wherein the causing of the at least one characteristic of the at least one portion of the device relative to the recipient to be visually indicated at least in part by overlaying the visual indication on a mapping of the recipient.

8. The system of claim 7, wherein the mapping is a three dimensional mapping of the recipient.

9. The system of claim 1, wherein the causing of the at least one characteristic of the at least one portion of the device relative to the recipient to be indicated at least in part by at least one of a visual indication, audio indication and haptic indication associated with extended reality.

10. The system of claim 1, further comprising at least one interrogation device in communication with the tracking device, the interrogation device configured to perform the interrogating of the at least one wireless tag.

11. A method for assessing at least one characteristic of a device within a recipient, the device being removably insertable into the recipient, the device including a treatment element, the treatment element including a balloon and a plurality of electrodes configured to deliver pulsed field ablation energy and at least one wireless tag embedded on an outer surface of the balloon, the method comprising:

when the device is inserted into the recipient, interrogating the at least one wireless tag, the interrogation of the at least one wireless tag indicating a distance between a plurality of the at least one wireless tag during expansion of the balloon;

receiving wireless data from the at least one wireless tag, the wireless data including treatment element data;

determining at least one characteristic of at least one portion of the device in three dimensional space based at least in part on the interrogation of the at least one wireless tag; and causing the at least one characteristic of the at least one portion of the device relative to the recipient to be indicated.

12. The method of claim 11, further comprising determining at least one of an impedance quantity and distance between wireless tags by assessing a signal strength and response time.

13. The method of claim 12, wherein the impedance quantity between the wireless tags corresponds to an indication of a quality of therapy.

14. The method of claim 11, wherein the determining the at least one characteristic of the at least one portion of the device in three dimensional space includes determining an orientation of the at least one portion of the device based at least in part on the interrogation.

15. The method of claim 11, wherein the determining of the at least one characteristic of the at least one portion of the device in three dimensional space includes determining a position of the treatment element of the device based at least in part on the interrogation.

16. The method of claim 11, further comprising determining an orientation between components of the device based at least in part on the interrogation.

17. The method of claim 11, wherein the causing of the at least one characteristic of the at least one portion of the device relative to the recipient to be visually indicated at least in part by overlaying the visual indication on a mapping of the recipient.

18. The method of claim 17, wherein the mapping is a three dimensional mapping of the recipient.

19. The method of claim 11, wherein the causing of the at least one characteristic of the at least one portion of the device relative to the recipient to be indicated at least in part by at least one of a visual indication, audio indication and haptic indication associated with extended reality.

20. The method of claim 11, wherein at least one interrogation device is in communication with the tracking device, the interrogation device configured to perform the interrogating of the at least one wireless tag.

* * * * *